(12) United States Patent
Martin

(10) Patent No.: US 6,319,927 B1
(45) Date of Patent: Nov. 20, 2001

(54) METHOD OF USING LEVOCETIRIZINE AND PHARMACEUTICAL COMPOSITIONS CONTAINING THE SAME FOR INDUCING SLEEP

(75) Inventor: Peter Martin, Far Hills, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 09/858,678

(22) Filed: May 16, 2001

Related U.S. Application Data

(63) Continuation of application No. 09/688,313, filed on Oct. 13, 2000, now Pat. No. 6,258,814.

(51) Int. Cl.$^7$ ................................................. A61K 31/495
(52) U.S. Cl. .......................................................... 514/252.12
(58) Field of Search ......................................... 514/252.12

(56) References Cited

U.S. PATENT DOCUMENTS 6,258,814 * 7/2001 Martin ............................. 514/252.12

* cited by examiner

*Primary Examiner*—Raymond Henley, III
(74) *Attorney, Agent, or Firm*—Robert J. Lipka

(57) ABSTRACT

Disclosed is a method of inducing sleep in a human suffering from a sleeping disorder comprising administering to the human a therapeutically effective amount of cetirizine hydrochloride once daily. Also disclosed is pharmaceutical compositions concerning the same.

24 Claims, No Drawings

METHOD OF USING LEVOCETIRIZINE AND PHARMACEUTICAL COMPOSITIONS CONTAINING THE SAME FOR INDUCING SLEEP

CROSS REFERENCE TO RELATED APPLICATION

The following application is a continuation of, and claims benefit of priority pursuant to 35 U.S.C. §120 to U.S. patent application Ser. No. 09/688,313, filed on Oct. 13, 2000, now U.S. Pat. No. 6,258,814.

FIELD OF THE INVENTION

The present invention relates to treating and/or preventing sleep disorders in a human by administering a therapeutically effective amount of cetirizine or a pharmaceutically acceptable salt thereof, and pharmaceutical compositions therefor.

BACKGROUND OF THE INVENTION

Sleep disorders are becoming increasingly prevalent in our society. It is estimated that 40 million Americans suffer from various sleep disorders. Further, 25 million more Americans suffer from intermittent-sleep-related disorders. Sleep disorders have various etiologies including stress induced by environmental and life style factors, physical factors, such as disease or obesity, and psychiatric disorders, such as depression.

Sleep disorders encompass, among other things, snoring, sleep apnea, insomnia, narcolepsy, restless legs syndrome, sleep terrors, sleep walking and sleep eating. Possible treatment can be as simple as behavior modification or it can be as involved as mechanical, surgical, or pharmacological intervention.

A particularly insidious sleep disorder is insomnia. Insomnia is defined as either having a difficulty falling asleep or overly frequent night awakenings. Insomnia can be caused by a number of different things including a change in environment, daily stress, caffeine, and other stimulants.

If left untreated, insomnia can adversely affect the quality of one's life. People with insomnia tend to suffer more frequently from depression and anxiety. Insomnia can also leave one tired and unable to perform at the workplace and/or even carry out normal daily activities. This inability to perform these activities has a negative impact on both professional and family life.

Typically, insomnia can be treated pharmacologically. Sedative hypnotics such as barbiturates, benzodiazepines and related compounds have been administered to treat insomnia. However, these compounds have a drawback because of the potential for addiction.

Sedating anti-histamine drugs have also been administered to treat insomnia. Agents such as diphenhydramine and hydroxyzine are typically administered due to their sedating properties. A second generation anti-histamine, ceterizine, is the primary acid metabolite of hydroxyzine resulting from the complete oxidation of hydroxyzine in vivo.

It has been reported that cetirizine may cause drowsiness when administered to patients. For instance, somnolence has been reported as the most frequently occurring side effect of cetirizine administration. Physician's Desk Reference, 2000 edition. Similarly, it has been reported that cetirizine impairs performance in tracking tests and increased both objective and subjective sleepiness in subjects. Nicholson AN, et al., *Aviat. Space Environ. Med.,* 1998 February; 69(2): 166–71.

Additionally, cetirizine has been reported to cause acute sedative activity by impairing driving performance and altering EEG energy spectra in the direction of electrocortical deactivation. Ramaeckers, et al., *Eur. J. Clin. Pharmacol.,* 1992, 42: 363–369.

None of the aforementioned references discloses the use of cetirizine to treat sleep disorders, particularly insomnia. In fact, in all of these studies, cetirizine induced drowsiness was considered an unwanted side effect.

SUMMARY OF THE INVENTION

The present invention provides a method of treating and/or preventing sleep disorders in a human comprising administering to a human a therapeutically effective amount of cetirizine or a pharmaceutically acceptable salt thereof. The present invention also provides pharmaceutical compositions containing cetirizine.

DETAILED DESCRIPTION OF THE INVENTION

The present inventions comprises a method for treating a human suffering from a sleeping disorder comprising administering to the human a therapeutically effective amount of cetirizine hydrochloride once daily.

The present invention also comprises a method for treating a human suffering from a sleep disorder comprising administering to the human a therapeutically effective amount of cetirizine hydrochloride once daily by oral or intranasal administration.

The present invention also comprises a method for treating a human suffering from a sleeping disorder comprising administering to the human a therapeutically effective amount of cetirizine hydrochloride once daily at least about 3 hours prior to a normal sleeping period.

The present invention also comprises a method for treating a human suffering from a sleep disorder comprising administering to the human a tablet formulation containing a therapeutically effective amount of cetirizine hydrochloride once daily by oral administration.

The present invention also comprises a pharmaceutical composition for intranasal administration comprising an amount of cetirizine or a pharmaceutically acceptable salt thereof that is sufficient to induce sleep in a human and an aqueous carrier comprising 70 to 90% by weight/volume of water; 0.10 to 5.00% by weight, volume of an aromatic alcohol; 0.01 to 0.3% by weight/volume of a non-mercurial antimicrobial preservative; 0 to 10% by weight/volume of a moisturizing agent; 0 to 10% by weight/volume of an antioxidant; 0 to 2.00% by weight/volume of a surfactant, a sufficient amount of a pharmaceutically acceptable buffer to maintain the pH of the composition within the range of about 3 to about 7; and QS water.

The present invention is particularly effective in treating and/or preventing sleep disorders in a patient suffering from disordered sleep. The terms "sleep disorders" and "disordered sleep" as used herein mean disordered, interrupted or fragmented sleep characterized by events including, but not limited to, snoring, periods of sleep apnea, insomnia, narcolepsy, restless legs syndrome, sleep terrors, sleep walking, sleep eating and daytime somnolence. The magnitude of a prophylactic or therapeutically effective dose of cetirizine in the acute or chronic management of sleep disorders will vary with the severity of the condition to be treated. The therapeutically effective amount, and perhaps the frequency, will also vary according to the age, body weight, and response of the individual patient.

The invention also includes the enantiomers, isomers and derivatives oc seterizine, preferably levocetirizine and dextrocetirizine, most preferably levocetirizine.

Cetirizine hydrochloride is an $H_1$-receptor antagonist. The chemical name is (±)-[2- [4-[(4-chlorophenyl) phenylmethyl]-1-piperazinyl]ethoxy]acetic acid, dihydrochloride. Cetirizine hydrochloride is a racemic compound with an empirical formula of $C_{21}H_{25}ClN_2O_3 \cdot 2HCl$. Cetirizine hydrochloride is a white, crystalline powder and is water soluble. Cetirizine hydrochloride is available from Pfizer Inc., New York, N.Y., under the trade name ZYRTEC®.

In general, the total daily therapeutically effective amount, for the conditions described herein, is from about 1 mg to about 40 mg of cetirizine administered in a single daily dose. For example, a preferred daily dose should be from about 10 mg to about 30 mg, most preferably one daily dose of about 20 mg.

The therapeutically effective dose to be administered is administered at least about 3 hours prior to a normal sleeping period, preferably about three to about 8 hours prior to a normal sleeping period, more preferably about four to about 6 hours prior to a normal sleeping period, and most preferably about 5 hours prior to a normal sleeping period.

As used herein, the term "normal sleeping period" means any time that a patient wishes to fall asleep. The term "normal" is in no way meant to limit the invention to any particular time of the day and/or night since patients have different lifestyles necessitating different times of administration.

The methods of the present invention may be carried out by administering pharmaceutical compositions containing cetirizine. Such compositions may be formulated by combining cetirizine or an equivalent amount of a pharmaceutically acceptable salt thereof with a suitable, inert, pharmaceutically acceptable carrier or diluent that is a solid or a liquid. Cetirizine may be converted into the pharmaceutically acceptable acid addition salts by admixing it with an equivalent amount of a pharmaceutically acceptable acid. Typically suitable pharmaceutically acceptable acids include the mineral acids, e.g., $HNO_3$, $H_2SO_4$, $H_3PO_4$, HCl, HBr, organic acids, including, but not limited to, acetic, trifluoroacetic, propionic, lactic, maleic, succinic, tartaric, glucuronic and citric acids as well as alkyl or arylsulfonic acids, such as p-toluenesulfonic acid, 2-naphthalenesulfonic acid, or methanesulfonic acid. The preferred pharmaceutically acceptable salt for use in the present invention is the chloride.

The compositions for carrying out the method claims of the instant invention may be solid form preparations including tablets, dispersible granules, capsules, cachets and suppositories. The powders and tablets may be comprised of from about 5 to about 70 percent active ingredient. Suitable solid carriers are known in the art, e.g. magnesium carbonate, magnesium stearate, talc, sugar, lactose. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas.

Preferably the compound is administered orally, intranasally or rectally.

Examples of pharmaceutically acceptable carriers and methods of manufacture for various compositions that are to be administered may be found in A. Gennaro (ed.), Remington's Pharmaceutical Sciences, 18th Ed., Mack Publishing Co., Easton, Pa.

The present invention also provides an aqueous, topical nasal composition comprising an amount of cetirizine or a pharmaceutically acceptable salt thereof sufficient to induce drowsiness and an aqueous carrier that is free of mercurial preservatives. The aqueous topical nasal sleep inducing composition comprises an amount of cetirizine or a pharmaceutically acceptable salt thereof sufficient to induce sleepiness and an aqueous carrier comprising: 70 to 90% by weight/volume of water; 0.10 to 5.00% by weight/volume of an aromatic alcohol; 0 to 0.3% by weight/volume of a non-mercurial anti-microbial preservative; 0 to 10% by weight/volume of a moisturizing agent; 0 to 0.10% by weight/volume of an antioxidant and a sufficient amount of a pharmaceutically acceptable buffer to maintain the pH of the composition within the range of about 3.00 to about 7.00; and QS water.

The present invention further provides a method of treating sleep disorders by administering to the nasal passage of a patient with a sleep disorder an aqueous topical composition of the present invention.

The amount of cetirizine or pharmaceutically acceptable salt thereof found in the aqueous topical composition of the present invention is in the range of about 1% to about 40% by weight/volume of the topical nasal composition, more preferably about 5% to about 10%, and most preferably 10%. Typically, 1% by weight/volume of cetirizine (as the HCl salt) is suitable for adults and children above five years of age.

The compositions of the present invention may contain an aromatic alcohol selected from the group consisting of benzyl alcohol and phenyl ethyl alcohol. The amount of aromatic alcohol present in the composition is from about 0.10 to 5.00% by weight/volume of the total composition. Ranges of 0.20–3.00% by weight/volume of the total composition are particularly suitable, and a range of 0.25 to 1.00% by weight/volume of the total composition is most preferable.

The compositions of the present invention may contain a surfactant, e.g. polysorbate 80. The amount of surfactant present in the composition is from about 0 to 2.00% by weight/volume of the total composition. Ranges of 0 to 1.50% by weight/volume of the total composition are particularly suitable, and a range of 0 to 1.25% by weight/volume of the total composition is most preferable.

The compositions of the present invention may contain moisturizing agents, e.g. propylene glycol. The amount of moisturizing agent present in the composition is from about 0 to 10.00% by weight/volume of the total composition. Ranges of 1.00 to 4.00% by weight/volume of the total composition are particularly suitable, and a range of 1.5 to 3.50% by weight/volume of the total composition is most preferable.

The compositions of the present invention may contain an antioxidant, e.g. disodium EDTA. The amount of antioxidant present in the composition is from about 0 to 0.10% by weight/volume of the total composition. Ranges of 0.01 to 0.05% by weight/volume of the total composition are particularly suitable, and a range of 0.015 to 0.030% by weight/volume of the total composition is most preferable.

The compositions of the present invention may contain at least one antimicrobial preservative in the range of 0.01% to about 0.3% by weight/volume of the composition. Typical suitable preservatives function as antimicrobial agents and include the commercially available preservatives, e.g. benzalkonium chloride in the range of about 0.02 to about 0.025% by weight/volume.

The compositions of the present invention may also include pharmaceutically acceptable buffers sufficient to adjust and maintain the pH of the compositions of the present invention in the range of about 3.0 to about 7.0, or more, preferably about 4.0 to about 5.0. Typically suitable buffers include citrate, phosphate and glycine.

The nasal spray composition of the present invention is manufactured in a conventional manner by thoroughly mixing the ingredients at ambient or elevated temperatures in order to achieve solubility of ingredients where appropriate.

All percentages are by weight/volume. The definitions of components whose chemical composition is not immediately clear from the name used, such as "Polysorbate 80", may be found in the CTFA Cosmetic Ingredients Dictionary, 4th Edition, 1991, published by Cosmetic Toiletry and Fragrance Association, Inc., Washington, D.C.

The following examples describe in detail the invention. It will be apparent to those skilled in the art that modifications may be practiced without departing from the purpose and intent of this disclosure.

EXAMPLE 1

An example of a tablet containing cetirizine for oral administration is as follows:

| Compound | Amount |
| --- | --- |
| Cetirizine HCl | 10 mg |
| Lactose | 60 mg |
| Mg stearate | 1 mg |

The preparation of the tablet is made according to methods that are well known to those of skill in the art and as disclosed in U.S. Pat. No. 4,525,358, which is herein incorporated by reference.

EXAMPLE 2

A second example of a tablet containing cetirizine for oral administration is as follows:

| Compound | Amount |
| --- | --- |
| Cetirizine HCl | 20 mg |
| Lactose | 57 mg |
| Mg stearate | 1 mg |

The preparation of the tablet is made according to methods that are well known to those of skill in the art.

EXAMPLE 3

Manufacture of Aqueous Nasal Spray

| Ingredients | % Wt./Vol. |
| --- | --- |
| Water USP purified | 80.0000 |
| Sodium phosphate monobasic | 0.5525 |
| Sodium phosphate dibasic | 0.0975 |
| Disodium EDTA | 0.0200 |
| Benzyl alcohol | 1.0000 |
| Benzalkonium chloride (17% solution) | 0.1177 |
| Propylene glycol USP | 3.5000 |
| Polysorbate 80 NF (Tween 80) | 1.2500 |
| Cetirizine hydrochloride | 1.0000 |
| Water USP purified | QS |

Method of Preparation

To any appropriate reaction container, add the following: sodium phosphate monobasic, sodium phosphate dibasic, disodium EDTA, benzyl alcohol and cetirizine hydrochloride to 70% of the water at a temperature of 50° C. Continue mixing the aqueous mixture while cooling to 30° C.

In a separate container, add 10% of the water, polysorbate 80 and the propylene glycol and mix the solution at 30° C. for at least 5 minutes. Transfer the contents of step 2 into the aqueous mixture of step 1. While mixing, add the benzalkonium chloride 17% solution to the aqueous mixture and mix for at least 5 minutes. Adjust the final batch volume with water, mix until uniform and then filter.

EXAMPLE 4

Aqueous Nasal Spray

| Ingredients | % Wt./Vol. |
| --- | --- |
| Water USP purified | 80.0000 |
| Sodium phosphate monobasic | 0.5525 |
| Sodium phosphate dibasic | 0.0975 |
| Disodium EDTA | 0.0200 |
| Benzyl alcohol | 0.2500 |
| Benzalkonium chloride (17% solution) | 0.1177 |
| Propylene glycol USP | 1.5000 |
| Polysorbate 80 NF (Tween 80) | 0.1500 |
| L-Menthol USP | 0.0900 |
| Eucalyptol | 0.0300 |
| Cetirizine hydrochloride | 1.0000 |
| Water USP purified | QS |

The procedure for preparation of this composition is as described in Example 3.

EXAMPLE 5

| Ingredients | % Wt./Vol. |
| --- | --- |
| Water USP purified | 80.0000 |
| Sodium phosphate monobasic | 0.5525 |
| Sodium phosphate dibasic | 0.0975 |
| Disodium EDTA | 0.0200 |
| Benzyl alcohol | 0.2500 |
| Benzalkonium chloride (17% solution) | 0.1177 |
| Propylene glycol USP | 1.5000 |
| Polysorbate 80 NF (Tween 80) | 0.1500 |

-continued

| Ingredients | % Wt./Vol. |
| --- | --- |
| Cetirizine hydrochloride | 1.0000 |
| Water USP purified | QS |

The procedure for preparation of this composition is as described in Example 3.

EXAMPLE 6

| Ingredients | % Wt./Vol. |
| --- | --- |
| Water USP purified | 80.0000 |
| Sodium phosphate monobasic | 0.5525 |
| Sodium phosphate dibasic | 0.0975 |
| Disodium EDTA | 0.0200 |
| Benzyl alcohol | 0.2500 |
| Benzalkonium chloride (17% solution) | 0.1177 |
| Propylene glycol USP | 1.5000 |
| Cetrizine hydrochloride | 1.0000 |
| Water USP purified | QS |

The procedure for preparation of this composition is as described in Example 3.

The patient treated in accordance with the methods of the present invention will enjoy uninterrupted sleep and will experience improved personal performance and workplace productivity.

I claim:

1. A method for inducing sleep in a human suffering from a sleeping disorder comprising administering to the human a therapeutically effective amount of levocetirizine or a pharmaceutically acceptable salt thereof once daily.

2. The method according to claim 1, wherein the amount of levocetirizine or a pharmaceutically acceptable salt thereof that is administered is from about 1 mg to about 40 mg.

3. The method according to claim 2, wherein the amount of levocetirizine or a pharmaceutically acceptable salt thereof that is administered is from about 10 mg to about 30 mg.

4. The method according to claim 3, wherein the amount of levocetirizine or a pharmaceutically acceptable salt thereof that is administered is about 20 mg.

5. The method according to claim 1, wherein the levocetirizine or a pharmaceutically acceptable salt thereof is administered at least about 3 hours prior to a normal sleeping period.

6. The method according to claim 5, wherein the levocetirizine or a pharmaceutically acceptable salt thereof is administered from about 3 hours to about 8 hours prior to a normal sleeping period.

7. The method according to claim 6, wherein the levocetirizine or a pharmaceutically acceptable salt thereof is administered from about 4 hours to about 6 hours prior to a normal sleeping period.

8. The method according to claim 7, wherein the levocetirizine or a pharmaceutically acceptable salt thereof is administered at about 5 hours prior to a normal sleeping period.

9. A method of inducing sleep in a human suffering from a sleep disorder comprising administering to the human a therapeutically effective amount of levocetirizine or a pharmaceutically acceptable salt thereof once daily by intranasal administration.

10. The method according to claim 9, wherein the amount of levocetirizine or a pharmaceutically acceptable salt thereof that is administered is from about 1 mg to about 40 mg.

11. The method according to claim 10, wherein the amount of levocetirizine or a pharmaceutically acceptable salt thereof that is administered is from about 10 mg to about 30 mg.

12. The method according to claim 11, wherein the amount of levocetirizine or a pharmaceutically acceptable salt thereof that is administered is about 20 mg.

13. The method according to claim 9, wherein the levocetirizine or a pharmaceutically acceptable salt thereof is administered at least about 3 hours prior to a normal sleeping period.

14. The method according to claim 13, wherein the levocetirizine or a pharmaceutically acceptable salt thereof is administered from about 3 hours to about 8 hours prior to a normal sleeping period.

15. The method according to claim 14, wherein the levocetirizine or a pharmaceutically acceptable salt thereof is administered from about 4 hours to about 6 hours prior to a normal sleeping period.

16. The method according to claim 15, wherein the levocetirizine or a pharmaceutically acceptable salt thereof is administered at about 5 hours prior to a normal sleeping period.

17. A method of inducing sleep in a human suffering from a sleeping disorder comprising administering to the human a therapeutically effective amount of levocetirizine or a pharmaceutically acceptable salt thereof once daily at least about 3 hours prior to a normal sleeping period.

18. The method according to claim 17, wherein the levocetirizine or a pharmaceutically acceptable salt thereof is administered at from about 3 hours to about 8 hours prior to a normal sleeping period.

19. The method according to claim 18, wherein the levocetirizine or a pharmaceutically acceptable salt thereof is administered at from about 4 hours to 6 hours prior to a normal sleeping period.

20. The method according to claim 19, wherein the levocetirizine or a pharmaceutically acceptable salt thereof is administered at about 5 hours prior to a normal sleeping period.

21. The method according to claim 17, wherein the amount of levocetirizine or a pharmaceutically acceptable salt thereof that is administered is from about 1 mg to about 40 mg.

22. The method according to claim 21, wherein the amount of levocetirizine or a pharmaceutically acceptable salt thereof that is administered is from about 10 mg to about 30 mg.

23. The method according to claim 22, wherein the amount of levocetirizine or a pharmaceutically acceptable salt thereof that is administered is about 20 mg.

24. A pharmaceutical composition for intranasal administration comprising an amount of levocetirizine or a pharmaceutically acceptable salt thereof that is sufficient to induce sleep in a human and an aqueous carrier comprising 70 to 90% by weight/volume of water; 0.10 to 5.00% by weight, volume of an aromatic alcohol; 0.01 to 0.3% by weight/volume of a non-mercurial antimicrobial preservative; 0 to 10% by weight/volume of a moisturizing agent; 0 to 10% by weight/volume of an antioxidant; 0 to 2.00% by weight/volume of a surfactant, a sufficient amount of a pharmaceutically acceptable buffer to maintain the pH of the composition within the range of about 3 to about 7; and QS water.

* * * * *